US011434193B2

(12) United States Patent
Ma et al.

(10) Patent No.: US 11,434,193 B2
(45) Date of Patent: Sep. 6, 2022

(54) PREPARATION METHOD FOR ESTERQUATS BASED ON OIL

(71) Applicant: EVONIK OPERATIONS GMBH, Essen (DE)

(72) Inventors: Guangyuan Ma, Shanghai (CN); Xiangyu Yang, Beijing (CN); Xiaoling Wang, Shanghai (CN); Hans Henning Wenk, Muelheim an der Ruhr (DE); Jiashu Wang, Shanghai (CN); Jianmin Xu, Shanghai (CN); Liang Bao, Shanghai (CN)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/255,857

(22) PCT Filed: Jun. 26, 2018

(86) PCT No.: PCT/CN2018/092810
§ 371 (c)(1),
(2) Date: Dec. 23, 2020

(87) PCT Pub. No.: WO2020/000172
PCT Pub. Date: Jan. 2, 2020

(65) Prior Publication Data
US 2021/0371373 A1 Dec. 2, 2021

(51) Int. Cl.
*C11D 3/30* (2006.01)
*C07C 213/06* (2006.01)
*C11D 3/00* (2006.01)
*D06M 13/463* (2006.01)

(52) U.S. Cl.
CPC ............ *C07C 213/06* (2013.01); *C11D 3/001* (2013.01); *C11D 3/30* (2013.01); *D06M 13/463* (2013.01); *D06M 2200/50* (2013.01)

(58) Field of Classification Search
CPC ......... C11D 1/62; C11D 3/0015; C11D 3/001; C11D 3/30; C11D 1/46; C07C 213/06
See application file for complete search history.

(56) References Cited

U.S. PATENT DOCUMENTS

| 4,830,771 | A | 5/1989 | Ruback et al. |
|---|---|---|---|
| 5,637,743 | A | 6/1997 | Contet et al. |
| 5,750,492 | A | 5/1998 | Contet et al. |
| 6,770,608 | B2 | 8/2004 | Franklin et al. |
| 7,214,718 | B1 | 5/2007 | Ohtawa et al. |
| 8,680,039 | B2 | 3/2014 | Lee et al. |
| 8,883,712 | B2 | 11/2014 | Kohle et al. |
| 9,745,251 | B2 | 8/2017 | Klostermann et al. |
| 10,618,867 | B2 | 4/2020 | Liebig et al. |
| 10,815,191 | B2 | 10/2020 | Schwab et al. |
| 2004/0076829 | A1* | 4/2004 | Levinson ............... C11D 1/835 428/411.1 |
| 2005/0022312 | A1* | 2/2005 | Bigorra Llosas .... C11D 3/0089 8/115.51 |
| 2011/0256083 | A1 | 10/2011 | Smith et al. |

FOREIGN PATENT DOCUMENTS

| CN | 101575299 | 11/2009 |
|---|---|---|
| EP | 1 884 560 | 3/2002 |
| KR | 20100036289 | 4/2010 |
| KR | 20120026325 | 3/2012 |

OTHER PUBLICATIONS

International Search Report for corresponding international application PCT/CN2018/092810 filed Jun. 26, 2018.
Written Opinion of the International Searching Authority for corresponding international application PCT/CN2018/092810 filed Jun. 26, 2018.
International Preliminary Report on Patentability for corresponding international application PCT/CN2018/092810 filed Jun. 26, 2018.
Supplementary European Search Report and Search Opinion for corresponding European application 18924719.

* cited by examiner

*Primary Examiner* — John R Hardee
(74) *Attorney, Agent, or Firm* — Law Office of: Michael A. Sanzo, LLC

(57) ABSTRACT

The present invention relates to a process for producing an esterquat by a transesterification reaction of a fatty acid oil or a mixture comprising one or more fatty acid oils and one or more fatty acids with a tertiary hydroxy amine and then a quaternization reaction. Esterquats obtained by the method of the invention show beneficial properties in particular when used as active component in fabric softener materials.

20 Claims, No Drawings

PREPARATION METHOD FOR ESTERQUATS BASED ON OIL

CROSS REFERENCE TO RELATED APPLICATIONS

The present application is US national stage of international application PCT/CN2018/092810, which had an international filing date of Jun. 26, 2018, and which was published on Jan. 2, 2020. The contents of the international application is hereby incorporated by reference herein in its entirety.

TECHNICAL FIELD

The present invention relates to a process for producing an esterquat by a transesterification reaction of one or more fatty acid oil or a mixture comprising one or more fatty acid oils and one or more fatty acids with a tertiary hydroxy amine and then a quaternization reaction. Esterquats obtained by the method of the invention show beneficial properties in particular when used as active component in fabric softener materials.

BACKGROUND ART

Trialkanolamine di fatty acid esters prepared by reaction of a trialkanolamine and a fatty acid were widely used as a fabric softener material after quaternization.

For example, U.S. Pat. No. 4,830,771 A disclosed preparation of triethanolamine di fatty acid esters by reacting triethanolamine with fatty acid methyl esters. However, the fatty acids to be used in preparing the above fabric softener materials are expensive.

KR 20100036289 A disclosed a method of preparing an esterquat by reacting a mixture of stearic acid and an oil with a hydroxyalkyl tertiary amine at high temperature and then quaternizing the resultant product. However, the above method has a complicated starting material. In addition, low molecular alcohol solvents were required in the quaternization reaction, which will result in undesirable side reactions generating unpleasant odor.

KR 2012026325 A disclosed that a fatty acid-containing oil and a tertiary hydroxyalkyl amine are reacted using an alkali catalyst and a phosphorus antioxidant, to obtain a fatty acid hydroxyalkyl amine ester. Then the ester is reacted with a quaternizing agent in a low-molecular alcohol solvent, to obtain a fiber softener. However, the low molecular alcohol solvent may react with the quaternizing agent, which result in bad colors and odors.

U.S. Pat. No. 8,680,039 B2 disclosed a fabric softener containing an esterquat, which was obtained by performing a two-step transesterification reaction of oil and tertiary hydroxyalkyl amine at low temperature in a high vacuum state under specific conditions, and then quaternizing the resultant product in a low-molecular alcohol solvent, which results in the disadvantage as KR 2012026325 A. In addition, the process is very complicated to handle. Besides, high vacuum is needed during the whole trans-esterification reaction.

U.S. Pat. No. 5,637,743 disclosed a method to produce quaternary ammonium surfactants derived from tertiary amines. In example 6, it particularly disclosed preparation of an esterquat from triethanolamine and partially hydrogenated palm oil under a nitrogen atmosphere. No information of the detailed composition of the transesterification reaction product or final product was disclosed.

In a fabric softener, both quaternized trialkanolamine di fatty acid ester (herein after diesterquat), preferably triethanolamine di fatty acid ester ("DEQ" or triethanolamine di fatty ester quat), and trialkanolamine mono fatty acid ester (herein after monoesterquat), preferably triethanolamine mono fatty ester ("MEQ", or triethanolamine mono fatty ester quat), are active compounds. Diesterquat has a better softening effect than monoesterquat. Quaternized trialkanolamine tri fatty acid ester (herein after triesterqauat), for example triethanolamine tri fatty ester ("TEQ", or triethanolamine tri fatty ester quat), is the inactive compound.

Reactions of trialkanolamine with fatty acids or with fatty acid oils followed by quaternization reactions, however, always lead to a mixture of mono-, di- and triesterquats. In the prior art methods described before the amount of triesterquat in the product mixture is relatively high.

Since mono- and diesterquats, in particular MEQ and DEQ, are the desired active components, a demand exists in the market for new production methods that are more selective to mono- and diesterquats, in particular MEQ and DEQ, and that reduce the amounts of the correlating triesterquats.

The problem of the invention, therefore, is to provide a new process to produce ester quats that does not have the problems of the prior art methods or that does have such problems only to a reduced degree.

In particular a method should be provided that has a higher selectivity to mono- and diesterquat, especially MEQ and DEQ, rather than to triesterquats, especially TEQ.

In a further special problem the new process should have economic benefits compared to the prior art processes, for example because of reduced raw material costs and/or reduced equipment costs and/or reduced operating costs.

Further problems not specifically mentioned become obvious in view of the subsequent description, examples and claims.

SUMMARY OF THE INVENTION

The inventors surprisingly found that the problems described before can be solved by a process according to claim 1. In particular they found out that a transesterification process of a hydroxy alkyl tertiary amine with a fatty acid oil or a mixture comprising one or more fatty acid oils and one or more fatty acids, wherein the addition of the oil or the mixture in at least two portions increases the selectivity of the reaction towards the target compounds such as triethanolamine mono fatty ester and triethanolamine di fatty ester and therefore increases the selectivity of the reaction toward mono- and diesterquats in the following quarternization step.

Beside of the higher selectivity, the process of the invention is beneficial because fatty acid oils are used instead of or in combination with a reduced amount of expensive fatty acids.

The inventors further found out that it is possible to conduct the transesterification reaction of the invention under atmospheric pressure, i.e. without vacuum conditions. This is of high economic benefit; equipment costs and operating cost can be reduced significantly compared to processes of the prior art.

As a further benefit the inventors found out that the reaction mixture of the inventive transesterification reaction can be used in the subsequent quaternization reaction without addition of any solvent, in particular without addition of any low-molecular weight alcohols. Formation of unwanted by-products as in the prior art processes can, thus, be avoided.

Other advantages of the present invention would be apparent for a person skilled in the art upon reading the specification.

The terms "oil" and "fatty acid oil" are used synonymously. They refer to fatty acid esters. Such oils comprise an alcohol component and a fatty acid component.

Each of the fatty acid component and the fatty acid used in the present invention comprises an alkyl carbonyl residue, i.e. comprises a C=O function as well as an alkyl chain that may be linear or branched and that may be saturated or unsaturated or partly hydrogenated.

As used herein, terms such as "comprise(s)" and the like as used herein are open terms meaning "including at least" unless otherwise specifically noted.

All references, tests, standards, documents, publications, etc. mentioned herein are incorporated herein by reference. Where a numerical limit or range is stated, the endpoints are included. Also, all values and subranges within a numerical limit or range are specifically included as if explicitly written out.

The description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention provides a process for producing quaternary ammonium compounds of Formula I:

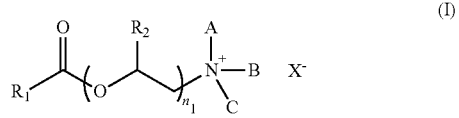

(I)

wherein A and B each independently represents $(CH_2CHR_2O)_{n2}H$ or $(CH_2CHR_2O)_{n3}OCR_3$; C represents methyl or ethyl or benzyl;

n1, n2 and n3 each independently represents an integer from 1 to 20, preferably 1-6, more preferred 1-3; most preferred 1 or 2 or 3; if A and B both are $(CH_2CHR_2O)_{n2}H$ or both are $(CH_2CHR_2O)_{n3}OCR_3$, n2 and n3 may be different or identical in A and B.

$R_2$ each independently represents H or an alkyl group selecting from the alkyl groups with from 1 to 6 carbon atoms, for example 1, 2, 3, 4, 5, or 6 carbon atoms, preferably from 1 to 3 carbon atoms; more preferred H, methyl or ethyl, even more preferred H or methyl, most preferred H;

$R_1$ and $R_3$ are each independently selected from the group consisting of linear or branched C7-C21, preferably C11-C21, more preferred C11-C19, most preferred C11-C17 alkyl groups, and linear or branched C7-C21, preferably C11-C21, more preferred C11-C19, most preferred C11-C17 alkenyl groups; and $X^-$ represents a counter ion used conventional in the art, preferably, an alkyl sulfate group such as $MeSO_4^-$ and $EtSO_4^-$, or a halide anion, preferably $Cl^-$, or an alkyl carbonate such as methyl carbonate and ethyl carbonate.

Preferably at least one of A and B represents $(CH_2CHR_2O)_{n2}H$, also preferred one of A and B represents $(CH_2CHR_2O)_{n2}H$ and the other represents $(CH_2CHR_2O)_{n3}OCR_3$; The method of the invention comprises a transesterification reaction step a) and a quaternization reaction step b).

In the transesterification step a) a hydroxy alkyl tertiary amine of Formula II

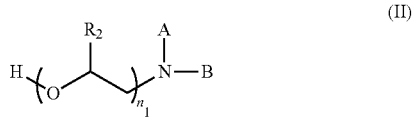

(II)

wherein A and B each independently represents $(CH_2CHR_2O)_{n2}H$ or $(CH_2CHR_2O)_{n3}H$ and wherein $n_1$, $n_2$, $n_3$ and $R_2$ are defined as for Formula I above, is reacted with one or more fatty acid oils or a mixture comprising one or more fatty acid oils and one or more fatty acids, wherein the alkyl or alkylene chains of the fatty acid residues correspond to $R_1$ and $R_3$ as defined for Formula I above.

The mixture comprising one or more fatty acid oils and one or more fatty acids is also referred to as "oil-acid mixture" in the present application.

Preferred examples of tertiary hydroxyalkyl amines according to Formula II of the invention may be selected from the group consisting of triethanolamine, ethanoldiisopropanolamine and any combinations thereof.

In quaternization step b) the reaction product of step a) is reacted with a quaternization agent C—X, wherein C and X are defined as for Formula I above, to obtain the quaternary ammonium compound of Formula I.

Preferred quaternizing agents C—X are those conventionally used in the art, including but not limited to alkyl halides such as methyl chloride; benzyl halides such as benzyl chloride; dialkyl sulfates such as dimethyl sulfate; dialkyl carbonates such as dimethyl carbonate and diethyl carbonate, and combinations thereof.

In the process of the invention the total amount of the total fatty acid oil or the oil-acid mixture used in step a) is divided into two or more portions. While portion 1 (i.e. first portion) is added to the hydroxy alkyl tertiary amine of Formula II at the start of the transesterification reaction, portion 2 (i.e. second portion) and any further portion is added to the reaction mixture at a later stage, i.e. after at least some, preferably around half, of the fatty acid oil or the oil-acid mixture of the first portion has reacted with the hydroxy alkyl tertiary amine. The fatty acid oil or the oil-acid mixture of the second or any further portion, thus, reacts with the remaining amount of the hydroxy alkyl tertiary amine.

In a preferred embodiment, the first portion of the fatty acid oil or the oil-acid mixture may accounts for 20-90 mol %, preferably 40-80 mol % of the total fatty acid oil or the oil-acid mixture ("total oil") used in the process.

It is preferred that in step a), molar ratio of the alkyl carbonyl group of the first portion of the fatty acid oil or the oil-acid mixture and the hydroxyalkyl tertiary amine according to Formula II at the time portion 1 is added is 0.3-2.4:1, preferably 0.9-2.1:1, even more preferably 1.2-1.8:1.

The second portion of the fatty acid oil or the oil-acid mixture is preferably added when the decrement of free hydroxyalkyl tertiary amine is more than 25 wt %, more preferred more than 40 wt %, even more preferred is 25-70 wt % and most preferred is 40-60 wt %, based on the initial amount of hydroxyalkyl tertiary amine.

The second or any further portion of the fatty acid oil or the oil-acid mixture may be added when the decrement of free hydroxyalkyl tertiary amine is more than 25%, for example, more than 30 wt %, 35 wt %, 40 wt %, 45 wt %, 50 wt %, 55 wt %, 60 wt %, 65 wt %, such as when the decrement of free hydroxyalkyl tertiary amine is 25-70 wt %, 25-65 wt %, 25-60 wt %, 25-55 wt %, 25-50 wt %, 25-45 wt %, 25-40 wt %, 30-70 wt %, 30-65 wt %, 30-60 wt %, 30-55 wt %, 30-50 wt %, 35-70 wt %, 35-60 wt %, 35-55 wt %, preferably more than 40 wt %, for example more than 45 wt %, 50 wt %, or 55 wt %, based on the initial amount of hydroxyalkyl tertiary amine.

Preferably the molar ratio of the alkyl carbonyl group of the total fatty acid oil or the oil-acid mixture ("total oil") and hydroxyalkyl tertiary amine in the process of the invention is 0.9-3.0:1, preferably 1.8-2.4:1.

It is preferred that in step a) the second or any further portion of the fatty acid oil or the oil-acid mixture, in sum, and a hydroxyalkyl tertiary amine according to formula II are reacted in a molar ratio of 0.3-1.5:1, preferably 0.6-0.9:1.

In the present invention, it should be understood that the remaining amount of the fatty acid oil or the oil-acid mixture after portion 1 can be added as one second portion or in two or more portions in two or more times into the transesterification reaction step. For example, the remaining amount of the fatty acid oil or the oil-acid mixture may be added in two times wherein each time accounts for 50% of the remaining amount.

Preferred classes of oils used in the present invention include triglyceride oil, diglyceride oils and monoglyceride oils. Preferred triglyceride oils are of plant or animal origin. Especially preferred are palm oil, palm kernel oil, coconut oil, olive oil, rapeseed oil, sunflower oil, cottonseed oil, jatropha oil or soy bean oil or mixtures thereof. Preferred animal oil is tallow, especially beef tallow.

Preferably the oils used in the present invention have iodine values (IV), i.e. degrees of saturation, in a range of from 0 to 150, preferably 0 to 80.

In a preferred embodiment of the present invention oils with different iodine values (IV) are used as portion 1 and as portion 2 or any of the further portions. This allows to fine tune for example softening properties and melting points of the resulting ester quats.

If for example the oil used as a first portion has a lower iodine value than the oil used as second portion, it is ensured that most of the fatty acids of the oil with the lower iodine value could be transferred to the trialkanolamine fatty ester. This is beneficial for softer applications because ester quats comprising fatty acids with lower IV provide better softness than ester quats comprising fatty acids with higher iodine value. Furthermore it can be ensured that only a part of the oil with higher IV is transferred to triethanolamine fatty ester and the rest exists as monoglyceride and diglyceride. Compounds obtained this way could provide lower melting point in the final quaternized product. Products obtained by such process are beneficial in view of softness and relatively low melting point compared to products obtained by a process where the same oils were mixed and then reacted at once with the trialkanolamine.

If glyceride oils are used, it is preferred not to separate or to remove all or parts of the glycerin or glycerides remaining in the reaction solution. Thus, the number of process steps can be reduced. This finding was unexpected since in the prior art processes glycerin had to be removed to shift the equilibrium of the reaction to the side of the alkanolamine fatty acid ester.

If no reaction products are removed from the reaction mixture in step a) no vacuum or low pressure conditions are required, which has additional economic benefits. This, however, does not exclude to apply such conditions during the reactions.

Surprisingly, the selectivity of the process of the invention to triealkanolamine di fatty ester, which is a more desirable target compound than trialkanolamine mono fatty ester, can be greatly improved when the transesterification reaction temperature in step a) is in the range of from 140 to 200 degree Celsius, preferably 140 to 180° C., more preferred 150 to 175° C., even more preferred 155 to 175° C., particular preferred 155 to 170° C., more particular preferred 160 to 170° C. and most preferred 162 to 168° C.

The transesterification reaction is preferably conducted under inert atmosphere, more preferred under nitrogen atmosphere, most preferred under nitrogen flow.

Preferably a catalyst is present in the reaction mixture during transesterification step a). Preferred catalysts are basic catalysts or metal oxide catalysts. More preferred catalysts are selected from the group consisting of sodium alkoxide catalysts such as sodium methoxide, sodium ethoxide, sodium propoxide, or sodium butoxide; titanium oxide catalysts such as titanium oxide; zinc oxide catalysts such as zinc oxide; alkali catalysts such as silica sodium hydroxide, potassium hydroxide, calcium hydroxide, anhydrous sodium carbonate, etc.; or sodium hypochlorite, etc., and any combinations thereof. Even more preferred catalysts are basic catalysts selected from alkali hydroxides, alkali alcohol salts, hypophosphite salts and mixtures thereof. Especially preferred catalysts are alkali alcohol salt and/or a hypophosphite salt, in particular sodium methoxide and/or sodium hypophosphite.

The amount of alkali alcohol salt in the reaction mixture is preferably in a range of from 0.1 to 0.3 wt %, and that of hypophosphite salt is in a range of from 0.05 to 0.2 wt % based on the total weight of the reaction mixture at the time.

In step b) of the process of the invention, i.e. the quaternization reaction step, it is preferred not to add any additional solvent.

In the present invention, "additional solvent" means any solvents added to facilitate the quaternization reaction. Examples are low molecular alcohol solvents typically used in the art, including but not limited to lower alcohols having 1 to 6 carbon atoms such as ethyl alcohol, propyl alcohol, isopropyl alcohol, etc; alkylene glycol having 1 to 6 carbon atoms such as ethylene glycol, diethylene glycol, propylene glycol, polyethylene glycol; glycerin and combinations thereof.

In another preferred embodiment step b) is conducted when the trialkanolamine content in the reaction mixture of step a) is below 5 wt. %, preferably between 0.5 and 4 wt. %, more preferred between 1 and 3.5 wt. %, even more preferred between 2 and 3.5 wt. %, most preferred between 3 and 3.5 wt %.

In an even more preferred embodiment step b) is conducted when the decrement of the trialkanolamine in the reaction mixture of step a) is more than 70 wt %, preferably more than 75 wt %, more preferred 80 wt %, even more preferred 85 wt %, most preferred more than 90 wt %, based on the initial amount of hydroxyalkyl tertiary amine in step a). The residue free hydroxyalkyl tertiary amine may be determined by gas chromatography (GC), with conventional protocols.

After the quaternization reaction step is completed, low molecular alcohol may optionally be introduced to the esterquat product as a solvent.

The quaternary ammonium compounds of Formula I may be used as a fabric softener material.

The invention further provides a fabric softener material which comprises ester quats prepared according to the process of the invention, preferably by a process that does not comprise any separate steps to remove glycerin.

The invention further provides a fabric softener product comprising the fabric softener material which is prepared according to the method of the invention, preferably by a process that does not comprise any separate steps to remove glycerin.

As mentioned above through the first addition of the triglyceride with lower iodine value and later addition of the triglyceride with higher iodine value, the softening properties of the final quaternized product may be improved and the melting point of the final quaternized product may be lowered.

Therefore, the present invention provides a method that can produce fabric softener material with increased selectivity to target compounds in the transesterification step.

The invention is now described in detail by the following examples. The scope of the invention should not be limited to the embodiments of the examples.

The NMR condition was as following: solvent 0.12 ml MeOD plus 0.48 ml CDCl$_3$; Bruker AVANCE III 500 MHz; relaxation delay: 3 s; scan number 8000.

EXAMPLE 1

Triethanolamine (326.6 g, 2.189 mol) and a first portion of oil, hardened palm oil (IV20, 880 g, 1.076 mol) were charged into a 2 L reactor. The mixture was heated and stirred at 80° C. for 0.5 hr under nitrogen atmosphere. The reactants were heated to 160° C. and stirred for 3 hrs after the addition of sodium hypophosphite (1.4 g) and sodium hydroxide (2.8 g). The extent of reaction was monitored by the content of residual triethanolamine, which was analyzed by GC. The composition of the fatty acid hydroxyl alkylamine ester reaction products was analyzed with H-NMR. The H-NMR results of a sample taken at 3 hs of reaction were shown in Table 1 below:

TABLE 1

| Components | Mol % | Components | Mol % |
|---|---|---|---|
| 1,2,3-triglyceride | 0 | TEA | 20 |
| 1,3-diglyceride | 5 | mono ester | 28 |
| 1,2-diglyceride | 3 | di ester | 23 |
| monoglyceride | 15 | tri ester | 6 |

When the GC results showed that the decrement of TEA was above 50 wt %, then the second portion of oil, hardened palm oil (IV20, 320 g, 0.391 mol) was charged into the 2 L reactor. The mixture was stirred 160° C. for 2.5 hrs. The composition of the fatty acid hydroxyl alkylamine ester reaction products was analyzed with H-NMR. The H-NMR results of a sample taken at 5.5 hs (3+2.5 hrs) of reaction were shown in Table 2 below.

TABLE 2

H-NMR results:

| Components | Mol % | Components | Mol % |
|---|---|---|---|
| 1,2,3-triglyceride | 0 | TEA | 13 |
| 1,3-diglyceride | 9 | mono ester | 22 |
| 1,2-diglyceride | 5 | di ester | 31 |
| monoglyceride | 15 | tri ester | 6 |

The first portion of the oil accounted for 73 mol % of the total oil used in the process.

When the GC results showed that the decrement of TEA was more than 75 wt %, the resulted ester (696.9 g, 0.99 mol) was charged into a 1 L reactor. The mixture was heated and stirred at 65° C. Then, dimethyl sulfate (122.2 g, 0.97 mol) was slowly introduced below 90° C. The reaction mixture was stirred for 0.5 hr after the addition of DMS. Propylene glycol (91 g) was added into reactor and stirred for another 0.5 hr.

As shown in the H-NMR results, the contents of the target compounds of the transesterification reaction: mono ester and di ester was 53 mol % based on the total molar amount of the composition, or 89.8 mol % based on the total molar amount of all triethanolamine fatty esters in example 1. In addition, the content of di ester was higher than that of mono ester.

COMPARATIVE EXAMPLE 1

Triethanolamine (157 g, 1.052 mol), hardened palm oil (IV20, 300 g, 0.367 mol) and hardened palm oil (IV45, 309 g, 0.367 mol) were charged into a 1 L reactor. The mixture was heated and stirred at 70° C. and the reactor was vacuumed and connected with nitrogen as inert-blanketing gas. Sodium methylate (25%, 5 g) was charged as the catalyst. Then, the reactants were heated to 140° C. and stirred for 4 hrs. The extent of reaction was monitored by the content of residual triethanolamine, which was analyzed by GC. The composition of the fatty acid hydroxyl alkylamine ester was analyzed with H-NMR. The H-NMR results of a sample taken at 4 hs of reaction were shown in Table 3 below:

TABLE 3

| Components | Mol % | Components | Mol % |
|---|---|---|---|
| 1,2,3-triglyceride | 1 | TEA | 12 |
| 1,3-diglyceride | 5 | mono ester | 22 |
| 1,2-diglyceride | 5 | di ester | 25 |
| monoglyceride | 20 | tri ester | 10 |

When the GC results showed that the decrement of TEA was 84.4 wt %, the resulted ester (242.8 g, 0.34 mol) was charged into a 500 mL reactor. The mixture was heated and stirred at 55° C. Then, dimethyl sulfate (41.9 g, 0.33 mol) was slowly introduced below 70° C. The reaction mixture was stirred for 1 hr after the addition of DMS. Propylene glycol (31.5 g) was added into reactor and stirred for another 0.5 hr. Sodium chlorite (30%, 0.9 g) was added for bleaching.

The contents of the target compounds mono ester and di ester was 47 mol % based on the total molar amount of the composition, or 82.4 mol % based on the total molar amount of all triethanolamine fatty esters.

EXAMPLE 2

Triethanolamine (157 g, 1.052 mol), hardened palm oil (IV20, 300 g, 0.367 mol) and hardened palm oil (IV45, 154.5 g, 0.184 mol) were charged into a 1 L reactor. The mixture was heated and stirred at 70° C. and the reactor was vacuumed and connected with nitrogen as inert-blanketing gas. Sodium methylate (25%, 5 g) was charged as the catalyst. The reactants were heated to 140° C. and stirred for 2 hrs. The extent of reaction was monitored by the content of residual triethanolamine, which was analyzed by GC. When the GC results showed that the decrement of TEA was more than 50 wt %, then the second portion of oil, hardened palm oil (IV45, 154.5 g, 0.184 mol) was charged into the reactor and the reaction mixture was stirred at 140° C. for another 2 hrs. The GC results of a sample taken at 4 hs of reaction showed that the decrement of TEA was 83.6 wt %.

The composition of the fatty acid hydroxyl alkylamine ester was analyzed with H-NMR. The H-NMR results of a sample taken at 4 hs of reaction were shown in Table 4 below:

TABLE 4

| Components | Mol % | Components | Mol % |
|---|---|---|---|
| 1,2,3-triglyceride | 2 | TEA | 12 |
| 1,3-diglyceride | 5 | mono ester | 26 |
| 1,2-diglyceride | 4 | di ester | 24 |
| monoglyceride | 19 | tri ester | 8 |

When the GC results showed that the decrement of TEA was 83.6 wt %, the resulted ester (242.8 g) was charged into a 500 mL reactor. The mixture was heated and stirred at 55° C. Then, dimethyl sulfate (41.9 g, 0.33 mol) was slowly introduced below 70° C. The reaction mixture was stirred for 1 hr after the addition of DMS. Propylene glycol (31.5 g) was added into reactor and stirred for another 0.5 hr. Sodium chlorite (30%, 0.9 g) was added for bleaching.

Table 5 shows the comparison between one step and two steps reaction regarding contents and selectivity of TEA esters according to example 2 and comparative example 1.

TABLE 5

| | Mono- and di-ester in total TEA ester (Mol %) | Tri-ester in total TEA ester (mol %) |
|---|---|---|
| Comparative example 1 | 82.46 | 17.54 |
| Example 2 | 86.21 | 13.79 |

As shown in Table 5, the selectivity of target compounds of the transesterification reaction, mono- and di-esters were higher in example 2 compared with comparative example 1.

As shown in the H-NMR results, the content of the target compounds of the transesterification reaction: mono ester and di ester was higher in example 2 (50 mol %) than that of comparative example 1 (47 mol %). In addition, the content of tri ester in example 2 was lower than that of comparative example 1.

COMPARATIVE EXAMPLE 2

Triethanolamine (78 g, 0.523 mol), hardened palm oil (IV20, 150 g, 0.183 mol) and hardened palm oil (IV45, 154.5 g, 0.183 mol) were charged into a 500 mL reactor. The mixture was heated and stirred at 70° C. and the reactor was vacuumed and connected with nitrogen as inert-blanketing gas. Sodium methylate (25%, 2.5 g) was charged as the catalyst. Then, the reactants were heated to 165° C. and stirred for 4 hrs. The extent of reaction was monitored by the content of residual triethanolamine, which was analyzed by GC. The composition of the fatty acid hydroxyl alkylamine ester reaction products was analyzed with H-NMR. The H-NMR results of a sample taken at 4 hs of reaction were shown in Table 6 below:

TABLE 6

| Components | Mol % | Components | Mol % |
|---|---|---|---|
| 1,2,3-triglyceride | 1 | TEA | 11 |
| 1,3-diglyceride | 4 | mono ester | 24 |
| 1,2-diglyceride | 7 | di ester | 23 |
| monoglyceride | 20 | tri ester | 10 |

When the GC results showed that the decrement of TEA was 83.4 wt %, the resulted ester (250.0 g) was charged into a 500 mL reactor. The mixture was heated and stirred at 55° C. Then, dimethyl sulfate (43.2 g, 0.34 mol) was slowly introduced below 70° C. The reaction mixture was stirred for 1 hr after the addition of DMS. Propylene glycol (31.4 g) was added into reactor and stirred for another 0.5 hr.

EXAMPLE 3

Triethanolamine (78 g, 0.523 mol), hardened palm oil (IV20, 150 g, 0.183 mol) and hardened palm oil (IV45, 77.3 g, 0.092 mol) were charged into a 500 mL reactor. The mixture was heated and stirred at 70° C. and the reactor was vacuumed and connected with nitrogen as inert-blanketing gas. Sodium hypophosphite 0.4 g (as color stabilizer) and sodium methylate (25%, 2.5 g) was charged as the catalyst. The reactants were heated to 165° C. and stirred for 2 hrs. The extent of reaction was monitored by the content of residual triethanolamine, which was analyzed by GC. When the GC results showed that the decrement of TEA was more than 50 wt %, then the second portion of oil, hardened palm oil (IV45, 77.3 g, 0.092 mol) was charged into the reactor and the reaction mixture was stirred at 165° C. for another 2 hrs. The GC results of a sample taken at 4 hs of reaction showed that the TEA content was 3.21 wt %.

The composition of the fatty acid hydroxyl alkylamine ester reaction products was analyzed with H-NMR. The H-NMR results of a sample taken at 4 hs of reaction were shown in Table 7 below:

TABLE 7

| Components | Mol % | Components | Mol % |
|---|---|---|---|
| 1,2,3-triglyceride | 2 | TEA | 10 |
| 1,3-diglyceride | 5 | mono ester | 21 |
| 1,2-diglyceride | 4 | di ester | 29 |
| monoglyceride | 21 | tri ester | 9 |

When the GC results showed that the decrement of TEA was 84.3 wt %, the resulted ester (117.9 g, 0.17 mol) was charged into a 500 mL reactor. The mixture was heated and stirred at 55° C. Then, dimethyl sulfate (20.5 g, 0.16 mol) was slowly introduced below 70° C. The reaction mixture was stirred for 1 hr after the addition of DMS. Propylene glycol (15.0 g) was added into reactor and stirred for another 0.5 hr.

Table 8 shows the comparison between one step and two steps reaction regarding contents and selectivity of TEA esters according to example 3 and comparative example 2.

TABLE 8

|  | Mono- and di-ester in total TEA ester (mol %) | Tri-ester in total TEA ester (mol %) |
| --- | --- | --- |
| Comparative example 2 | 82.46 | 17.54 |
| Example 3 | 84.75 | 15.25 |

As shown in Table 8, the selectivity of target compounds of the transesterification reaction, mono- and di-esters were higher in example 3 compared with comparative example 2.

In comparative example 2, the contents of the target compounds mono ester and di ester was 47 mol % based on the total molar amount of the reaction product of the transesterification reaction, in contrast, in example 3, the contents of the target compounds mono ester and di ester was 50 mol % based on the total molar amount of the reaction product of the transesterification reaction. Particularly, the most important target compounds of the transesterification reaction, di ester increased from 23 mol % in comparative example 2 to 29 mol % in example 3. The content of tri ester in example 3 was lower compared with that of comparative example 2.

EXAMPLE 4

Triethanolamine (62.8 g, 0.421 mol), hardened palm oil (IV20, 120 g, 0.147 mol) and hardened palm oil (IV45, 61.8 g, 0.073 mol) were charged into a 500 mL reactor. The mixture was heated and stirred at 70° C. and the reactor was vacuumed and connected with nitrogen as inert-blanketing gas. Sodium hypophosphite 0.3 g and sodium methylate (25%, 2.0 g) was charged as the catalyst. The reactants were heated to 150° C. and stirred for 2 hrs. The extent of reaction was monitored by the content of residual triethanolamine, which was analyzed by GC. When the GC results showed that the decrement of TEA was more than 50 wt %, then the second portion of oil, hardened palm oil (IV45, 77.3 g, 0.092 mol) was charged into the reactor and the reaction mixture was stirred at 150° C. for another 2 hrs. The GC results of a sample taken at 4 hs of reaction showed that the decrement of TEA was 84.3 wt %.

The composition of the fatty acid hydroxyl alkylamine ester reaction products was analyzed with H-NMR. The H-NMR results of a sample taken at 4 hs of reaction were shown in Table 9 below:

TABLE 9

| Components | Mol % | Components | Mol % |
| --- | --- | --- | --- |
| 1,2,3-triglyceride | 3.7 | TEA | 10.5 |
| 1,3-diglyceride | 5.5 | mono ester | 21.8 |
| 1,2-diglyceride | 3.5 | di ester | 26.5 |
| monoglyceride | 18.4 | tri ester | 10.2 |

EXAMPLE 5

Triethanolamine (62.8 g, 0.421 mol), hardened palm oil (IV20, 120 g, 0.147 mol) and hardened palm oil (IV45, 61.8 g, 0.073 mol) were charged into a 500 mL reactor. The mixture was heated and stirred at 70° C. and the reactor was vacuumed and connected with nitrogen as inert-blanketing gas. Sodium hypophosphite 0.3 g and sodium methylate (25%, 2.0 g) was charged as the catalyst. The reactants were heated to 180° C. and stirred for 2 hrs. The extent of reaction was monitored by the content of residual triethanolamine, which was analyzed by GC. When the GC results showed that the decrement of TEA was more than 50 wt %, then the second portion of oil, hardened palm oil (IV45, 77.3 g, 0.092 mol) was charged into the reactor and the reaction mixture was stirred at 180° C. for another 2 hrs. The GC results of a sample taken at 4 hs of reaction showed that the decrement of TEA was 86.5 wt %.

The composition of the fatty acid hydroxyl alkylamine ester reaction products was analyzed with H-NMR. The H-NMR results of a sample taken at 4 hs of reaction were shown in Table 10 below:

TABLE 10

| Components | Mol % | Components | Mol % |
| --- | --- | --- | --- |
| 1,2,3-triglyceride | 1.7 | TEA | 8.6 |
| 1,3-diglyceride | 6.0 | mono ester | 19.7 |
| 1,2-diglyceride | 3.2 | di ester | 29.3 |
| monoglyceride | 16.5 | tri ester | 15.1 |

EXAMPLE 6

Triethanolamine (62.8 g, 0.421 mol), hardened palm oil (IV20, 120 g, 0.147 mol) and hardened palm oil (IV45, 61.8 g, 0.073 mol) were charged into a 500 mL reactor. The mixture was heated and stirred at 70° C. and the reactor was vacuumed and connected with nitrogen as inert-blanketing gas. Sodium hypophosphite 0.3 g and sodium methylate (25%, 2.0 g) was charged as the catalyst. The reactants were heated to 200° C. and stirred for 2 hrs. The extent of reaction was monitored by the content of residual triethanolamine, which was analyzed by GC. When the GC results showed that the decrement of TEA was more than 50 wt %, then the second portion of oil, hardened palm oil (IV45, 77.3 g, 0.092 mol) was charged into the reactor and the reaction mixture was stirred at 200° C. for another 2 hrs. The GC results of a sample taken at 4 hs of reaction showed that the decrement of TEA was 86.5 wt %.

The composition of the fatty acid hydroxyl alkylamine ester reaction products was analyzed with H-NMR. The H-NMR results of a sample taken at 4 hs of reaction were shown in Table 11 below:

TABLE 11

| Components | Mol % | Components | Mol % |
| --- | --- | --- | --- |
| 1,2,3-triglyceride | 1.5 | TEA | 5.7 |
| 1,3-diglyceride | 6.5 | mono ester | 16.5 |
| 1,2-diglyceride | 2.9 | di ester | 35.2 |
| monoglyceride | 12.5 | tri ester | 19.3 |

It was surprising to found that the selectivity to the most important target compounds of the transesterification reaction, di ester in all the three esters (mono, di and tri esters) peaked at around the reaction temperature of 165° C. (see Table 12). The selectivity to di ester increased substantially when the reaction temperature increased from 150° C. to 165° C., and decreased substantially when the reaction temperature further increased to 180° C. Although the amount of di ester was higher in Example 6 than Example 3, the amount of tri ester which was an undesirable byproduct was much higher.

TABLE 12

|  | Example 4 | Example 3 | Example 5 | Example 6 |
|---|---|---|---|---|
| Reaction temperature (° C.) | 150 | 165 | 180 | 200 |
| mono ester | 21.8 | 21 | 19.7 | 16.5 |
| di ester | 26.5 | 29 | 29.3 | 35.2 |
| tri ester | 10.2 | 9 | 15.1 | 19.3 |
| Selectivity (mono + di)/total ester (%) | 82.6 | 84.7 | 76.4 | 72.8 |
| Selectivity (di)/total ester (%) | 45.30% | 49.15% | 45.71% | 49.58% |
| Selectivity (tri)/total ester (%) | 17.4% | 15.25% | 23.55% | 27.2% |
| mono + di esters | 48.3 | 50 | 49 | 51.7 |

The invention claimed is:

1. A process for producing a quaternary ammonium compound of Formula I:

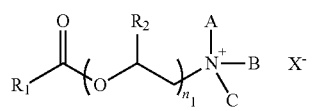

(I)

wherein A and B each independently represents $(CH_2CHR_2O)_{n2}H$ or $(CH_2CHR_2O)_{n3}OCR_3$; and C represents methyl, ethyl or benzyl;

n1, n2 and n3 each independently represents an integer from 1 to 20, wherein if A and B both are $(CH_2CHR_2O)_{n2}H$ or both are $(CH_2CHR_2O)_{n3}OCR_3$, n2 and n3 may be different or identical in A and B;

$R_2$ each independently represents H or an alkyl group with from 1 to 6 carbon atoms;

$R_1$ and $R_3$ are each independently selected from the group consisting of: linear or branched C7-C21 alkyl groups, and linear or branched C7-C21 alkenyl groups;

$X^-$ represents a counter ion;

and wherein the process comprises:

step a), wherein a hydroxy alkyl tertiary amine of Formula II

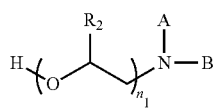

(II)

in which A and B each independently represents $(CH_2CHR_2O)_{n2}H$ or $(CH_2CHR_2O)_{n3}H$ and n1, n2, n3 and $R_2$ are defined as for Formula I above, is reacted with one or more fatty acid oils or a mixture comprising one or more fatty acid oils and one or more fatty acids, wherein the alkyl or alkylene chains of the fatty acid residues correspond to $R_1$ and $R_3$ as defined for Formula I above;

and wherein the process further comprises:

step b), wherein the reaction product of step a) is reacted with a quaternization agent C—X, in which C and X are defined as for Formula I above, to obtain the quaternary ammonium compound of Formula I;

wherein the total amount of the oils to be added in step a) is divided into at least two portions, wherein portion 1 is added to the hydroxy alkyl tertiary amine of Formula II at the start of step a) and portion 2, as well as any further portion, is added to the reaction mixture after at least some of the oil of portion 1 has reacted with the hydroxy alkyl tertiary amine according to Formula II.

2. The process of claim 1, wherein:
a) n1, n2 and n3 each independently represents an integer from 1-6;
b) $R_2$ is H, methyl or ethyl;
c) $R_1$ and $R_3$ are each independently selected from the group consisting of: linear or branched C11-C21 alkyl groups, and linear or branched C11-C21 alkenyl groups;
d) $X^-$ represents an alkyl sulfate group, a halide anion or an alkyl carbonate.

3. The process of claim 1, wherein:
a) n1, n2 and n3 each independently represents an integer from 1-3;
b) $R_2$ is H;
c) $R_1$ and $R_3$ are each independently selected from the group consisting of linear or branched C11-C17 alkyl groups and linear or branched C11-C17 alkenyl groups;
d) $X^-$ represents MeSO4-, EtSO4-, Cl—, methyl carbonate or ethyl carbonate.

4. The process of claim 1, wherein, in step a), the molar ratio of the alkyl carbonyl group of portion 1 of the fatty acid oil or the mixture comprising one or more fatty acid oils and one or more fatty acids and the hydroxyalkyl tertiary amine according to Formula II, at the time portion 1 is added, is 0.3-2.4:1.

5. The process of claim 1, wherein, when the decrement of free hydroxyalkyl tertiary amine according to Formula II is more than 25 wt % based on the initial amount of hydroxyalkyl tertiary amine, the portion 2 of the fatty acid oil or the mixture comprising one or more fatty acid oils and one or more fatty acids is added.

6. The process of claim 1, wherein the molar ratio of the alkyl carbonyl group of the total fatty acid oil or the mixture comprising one or more fatty acid oils and one or more fatty acids (total oil) and hydroxyalkyl tertiary amine is 0.9-3.0:1.

7. The process of claim 1, wherein the oil used in step a) is selected from the group consisting of: triglyceride oils; diglyceride oils; monoglyceride oils; or mixtures thereof.

8. The process of claim 1, wherein the oil added as portion 1 in step a) is different from the oil added as portion 2 or a further portion.

9. The process of claim 1, wherein the oil used as portion 1 has a lower iodine value than the oil used as portion 2 or a further portion.

10. The process of claim 1, wherein the tertiary hydroxyalkyl amines according to formula II are selected from the group consisting of: triethanolamine; ethanol diisopropanolamine; and combinations thereof.

11. The process of claim 1, wherein none or only a part of glycerin and/or glycerides are separated or removed from the reaction mixture; and/or the reaction in step a) and/or b) is conducted under an inert atmosphere; and/or no solvent is added in step b) before the quaternization reaction is conducted.

12. The method of claim 1, wherein a vacuum is not applied in step a).

13. The process of claim 1, wherein the temperature of the reaction mixture in step a) is in a range of from 140 to 180° C.

14. The process of claim 1, wherein the temperature of the reaction mixture in step a) is in a range of 162 to 168° C.

15. The process of claim 1, wherein the reaction mixture comprises an alkali catalyst during step a).

16. The process of claim 1, wherein the reaction mixture comprises a catalyst selected from the group consisting of: sodium alkoxide; titanium oxide; zinc oxide; an alkali catalyst; an alkali alcohol salt; a hypophosphite salt; and mixtures thereof.

17. The process of claim 16, wherein the catalyst is an alkali alcohol salt in a range of from 0.1 to 0.3 wt %, based on the total weight of the reaction mixture at the time.

18. The process of claim 1, wherein step b) is conducted when the decrement of the trialkanolamine in the reaction mixture of step a) is more than 70 wt %, based on the initial amount of hydroxyalkyl tertiary amine in step a).

19. A process of producing a fabric softener material comprising the reaction steps of claim 1.

20. A fabric softener material comprising esterquats prepared by the process of claim claim 1.

* * * * *